(12) United States Patent
Rao et al.

(10) Patent No.: US 12,708,432 B2
(45) Date of Patent: Aug. 18, 2026

(54) CATHETER INSTRUMENT WITH THREE PULL WIRES

(71) Applicant: Biosense Webster (Israel) Ltd., Yokneam (IL)

(72) Inventors: Anand R. Rao, Tustin, CA (US); Thanh V. Nguyen, El Monte, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 680 days.

(21) Appl. No.: 16/988,996

(22) Filed: Aug. 10, 2020

(65) Prior Publication Data

US 2021/0085386 A1 Mar. 25, 2021

Related U.S. Application Data

(60) Provisional application No. 62/903,337, filed on Sep. 20, 2019.

(51) Int. Cl.
*A61B 18/14* (2006.01)
*A61B 17/00* (2006.01)
(Continued)

(52) U.S. Cl.
CPC .................... *A61B 18/1492* (2013.01); *A61B 2017/00327* (2013.01); *A61B 2018/00029* (2013.01);
(Continued)

(58) Field of Classification Search
CPC ...... A61B 18/1492; A61B 2017/00327; A61B 1/0057; A61B 1/00078; A61M 25/0147; A61M 25/0144
See application file for complete search history.

(56) References Cited

U.S. PATENT DOCUMENTS 5,715,817 A * 2/1998 Stevens-Wright .......................... A61M 25/0147 604/95.04
5,738,096 A 4/1998 Ben-Haim
(Continued)

FOREIGN PATENT DOCUMENTS

EP 2289592 A2 3/2011
EP 3015064 A2 5/2016
(Continued)

OTHER PUBLICATIONS

U.S. Food & Drug Administration, “FDA-Cleared Sterilants and High Level Disinfectants with General Claims for Processing Reusable Medical and Dental Devices,” Mar. 2015, downloaded from https://www.fda.gov/medical-devices/reprocessing-reusable-medical-devices-information-manufacturers/fda-cleared-sterilants-and-high-level-disinfectants-general-claims-processing-reusable-medical-and, 7 pgs.

(Continued)

*Primary Examiner* — Jaymi E Della
(74) *Attorney, Agent, or Firm* — FBT Gibbons LLP

(57) ABSTRACT

An apparatus includes a handle, a catheter, and an end effector. The catheter extends distally from the handle. The catheter includes a body, a first cable, a second cable, and a third cable. The first cable is positioned in a first lumen of the catheter body and is operable to translate relative to the body of the catheter. The second cable is positioned in a second lumen of the catheter body and is operable to translate relative to the body of the catheter. The third cable is positioned in a third lumen of the catheter body and is operable to translate relative to the body of the catheter. The end effector extends distally from the catheter. The end effector includes at least one electrode.

7 Claims, 14 Drawing Sheets

(51) Int. Cl.
*A61B 18/00* (2006.01)
*A61M 25/01* (2006.01)

(52) U.S. Cl.
CPC ............... *A61B 2018/00214* (2013.01); *A61B 2018/00577* (2013.01); *A61B 2018/00636* (2013.01); *A61B 2018/0091* (2013.01); *A61B 2018/1467* (2013.01); *A61B 2218/002* (2013.01); *A61M 25/0144* (2013.01); *A61M 25/0147* (2013.01)

(56) References Cited

U.S. PATENT DOCUMENTS 5,928,191 A * 7/1999 Houser ............. A61M 25/0136 606/41
6,325,972 B1 12/2001 Jacobs et al.
6,365,102 B1 4/2002 Wu et al.
6,447,719 B1 9/2002 Agamohamadi et al.
6,852,277 B2 2/2005 Platt, Jr. et al.
6,852,279 B2 2/2005 Williams et al.
6,939,519 B2 9/2005 Agamohamadi et al.
7,591,799 B2 9/2009 Selkee
8,523,808 B2 9/2013 Selkee
8,956,353 B2 2/2015 Govari et al.
9,101,269 B2 8/2015 Selkee
9,101,733 B2 8/2015 McDaniel
9,314,299 B2 4/2016 Fang
9,480,416 B2 11/2016 Govari et al.
9,801,585 B2 10/2017 Shah et al.
9,907,480 B2 3/2018 Basu et al.
10,130,422 B2 11/2018 Ditter
10,561,753 B2 2/2020 Thompson et al.
10,660,700 B2 5/2020 Beeckler et al.
10,702,177 B2 7/2020 Aujla
10,743,932 B2 8/2020 Gallardo et al.
2001/0009986 A1 7/2001 Ponzi
2002/0077627 A1* 6/2002 Johnson ................. A61B 18/18 606/41
2002/0082584 A1 6/2002 Rosenman et al.
2013/0030426 A1* 1/2013 Gallardo ............ A61B 18/1492 606/41
2013/0046298 A1* 2/2013 Kaufman .......... A61M 25/0144 606/1
2013/0158379 A1* 6/2013 Selkee ................... A61B 18/00 604/95.04
2014/0114129 A1 4/2014 Peh et al.
2016/0113582 A1* 4/2016 Altmann ............ A61B 18/1492 606/41
2017/0042473 A1* 2/2017 Quinn .................. A61B 5/6858
2018/0071017 A1 3/2018 Bar-Tal et al.
2018/0272108 A1 9/2018 Padilla et al.
2019/0282223 A1 9/2019 Raybin et al.
2021/0106330 A1 4/2021 Burbank
2022/0339407 A1 10/2022 Matlock et al.
2023/0218863 A1 7/2023 Sarabia

FOREIGN PATENT DOCUMENTS

EP 3095482 A1 11/2016
JP 2019-013758 A 1/2019

OTHER PUBLICATIONS

U.S. Appl. No. 62/903,337, filed Sep. 20, 2019 by Rao et al., entitled: "Catheter Instrument With Three Pull Wires."
International Search Report and Written Opinion dated Feb. 3, 2021, for International Application No. PCT/IB2020/058493, 10 pages.
European Examination Report dated Oct. 5, 2023 for Application No. EP 20789662.2, 4 pgs.
Chinese Office Action, The First Office Action, and the First Search, dated Mar. 14, 2024 for Application No. CN 202080065553.9, 11 pgs.
Japanese Office Action dated Mar. 5, 2024, for Application No. JP 2022-517802, 6 pgs.
Chinese First Office Action and Search Report dated Feb. 27, 2024, for Application No. 202080065553.9, 17 pages.

* cited by examiner 200
250
230
110, 112

LA
300
120
122
172
170
160
162
180 x
y

CATHETER INSTRUMENT WITH THREE PULL WIRES

PRIORITY

This application claims priority to U.S. Provisional Pat. App. No. 62/903,337, entitled "Catheter Instrument with Three Pull Wires," filed Sep. 20, 2019, the disclosure of which is incorporated by reference herein in its entirety.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). The one or more electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad or other reference electrode that is in contact with the patient that is in contact with the patient. Irrigation may be used to draw heat from ablating components of an ablation catheter; and to prevent the formation of blood clots near the ablation site.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein, in its entirety; U.S. Pub. No. 2017/0312022, entitled "Irrigated Balloon Catheter with Flexible Circuit Electrode Assembly," published Nov. 2, 2017, the disclosure of which is incorporated by reference herein, in its entirety; U.S. Pub. No. 2018/0071017, entitled "Ablation Catheter with a Flexible Printed Circuit Board," published Mar. 15, 2018, the disclosure of which is incorporated by reference herein, in its entirety; U.S. Pub. No. 2018/0056038, entitled "Catheter with Bipole Electrode Spacer and Related Methods," published Mar. 1, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; U.S. Pat. No. 8,956,353, entitled "Electrode Irrigation Using Micro-Jets," issued Feb. 17, 2015, the disclosure of which is incorporated by reference herein, in its entirety; and U.S. Pat. No. 9,801,585, entitled "Electrocardiogram Noise Reduction," issued Oct. 31, 2017, the disclosure of which is incorporated by reference herein, in its entirety.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein, in its entirety. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein, in its entirety; U.S. Pat. No. 10,130,422, entitled "Catheter with Soft Distal Tip for Mapping and Ablating Tubular Region," issued Nov. 20, 2018, the disclosure of which is incorporated by reference herein, in its entirety; and U.S. Pub. No. 2018/0056038, entitled "Catheter with Bipole Electrode Spacer and Related Methods," published Mar. 1, 2018, the disclosure of which is incorporated by reference herein, in its entirety.

When using an ablation catheter, it may be desirable to ensure that the one or more electrodes of the ablation catheter are sufficiently contacting target tissue. For instance, it may be desirable to ensure that the one or more electrodes are contacting target tissue with enough force to effectively apply RF ablation energy to the tissue; while not applying a degree of force that might tend to undesirably damage the tissue. To that end, it may be desirable to include one or more force sensors or pressure sensors to detect sufficient contact between one or more electrodes of an ablation catheter and target tissue.

In addition to using force sensing or EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, California Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein, in its entirety; and various other references that are cited herein.

While several catheter systems and methods have been made and used, it is believed that no one prior to the inventors has made or used the invention described, illustrated and claimed herein.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms “about” or “approximately” for any numerical values or ranges indicate a suitable dimensional tolerance that allows the part or collection of components to function for its intended purpose as described herein. More specifically, “about” or “approximately” may refer to the range of values ±20% of the recited value, e.g. “about 90%” may refer to the range of values from 71% to 99%. In addition, as used herein, the terms “patient,” “host,” “user,” and “subject” refer to any human or animal subject and are not intended to limit the systems or methods to human use, although use of the subject invention in a human patient represents a preferred embodiment.

I. Overview of Example of a Catheter System

Figure 1:
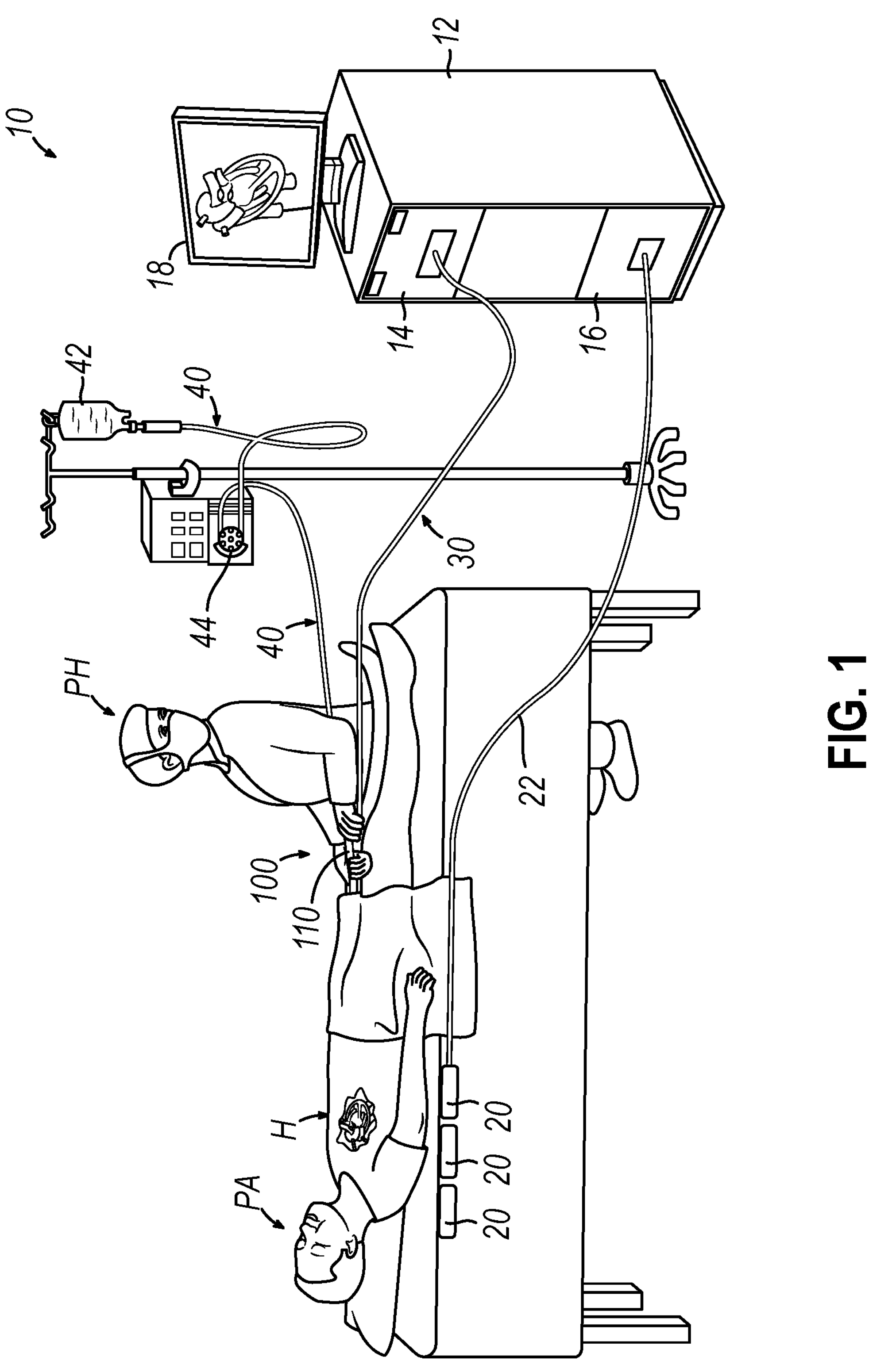
FIG. 1 depicts a schematic view of a medical procedure in which a catheter of a catheter assembly is inserted in a patient.
Figure 2A:
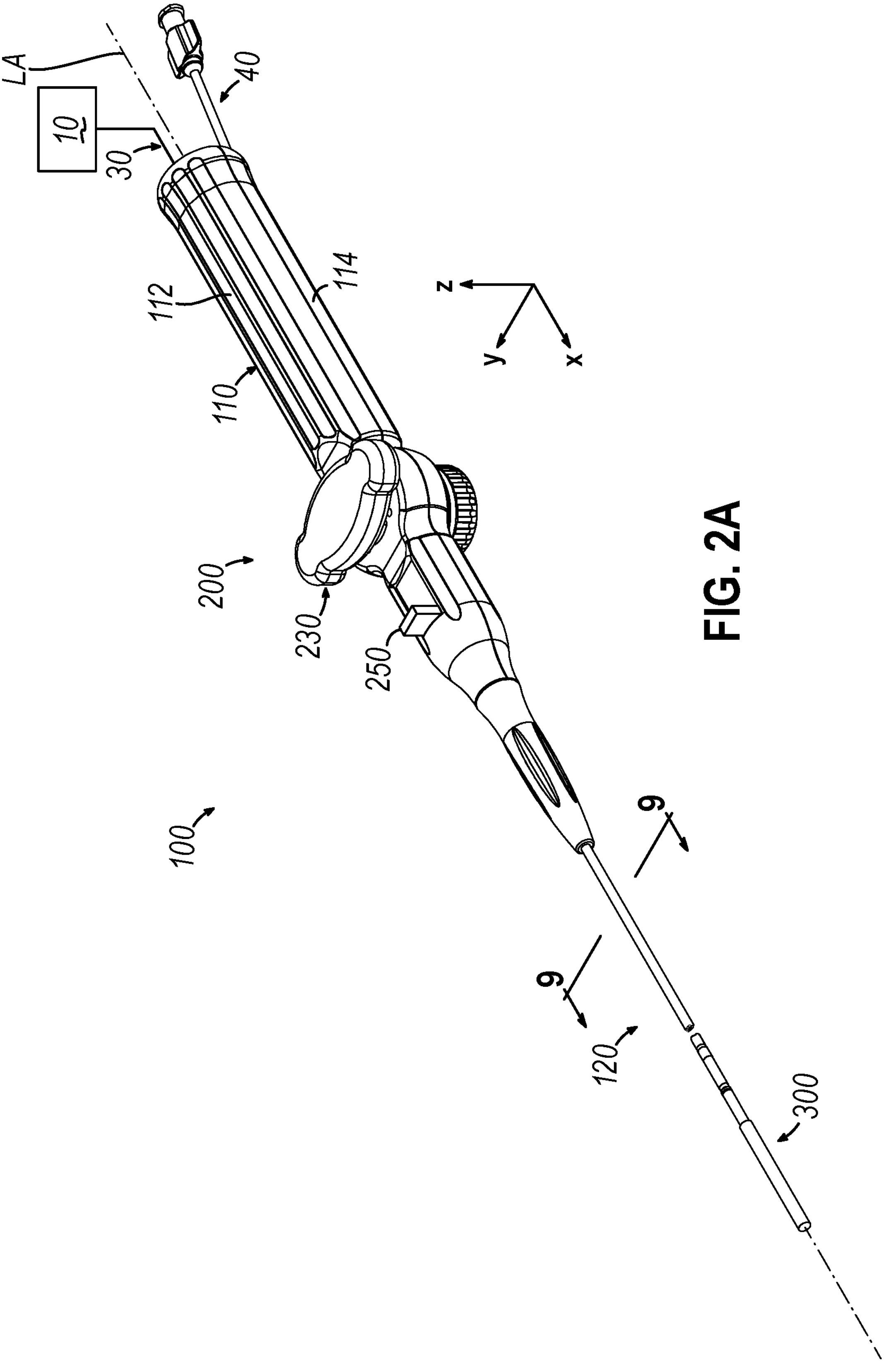
FIG. 2A depicts a perspective view of the catheter assembly of FIG. 1, with additional components shown in schematic form, and with an end effector in a non-expanded state.
Figure 2B:
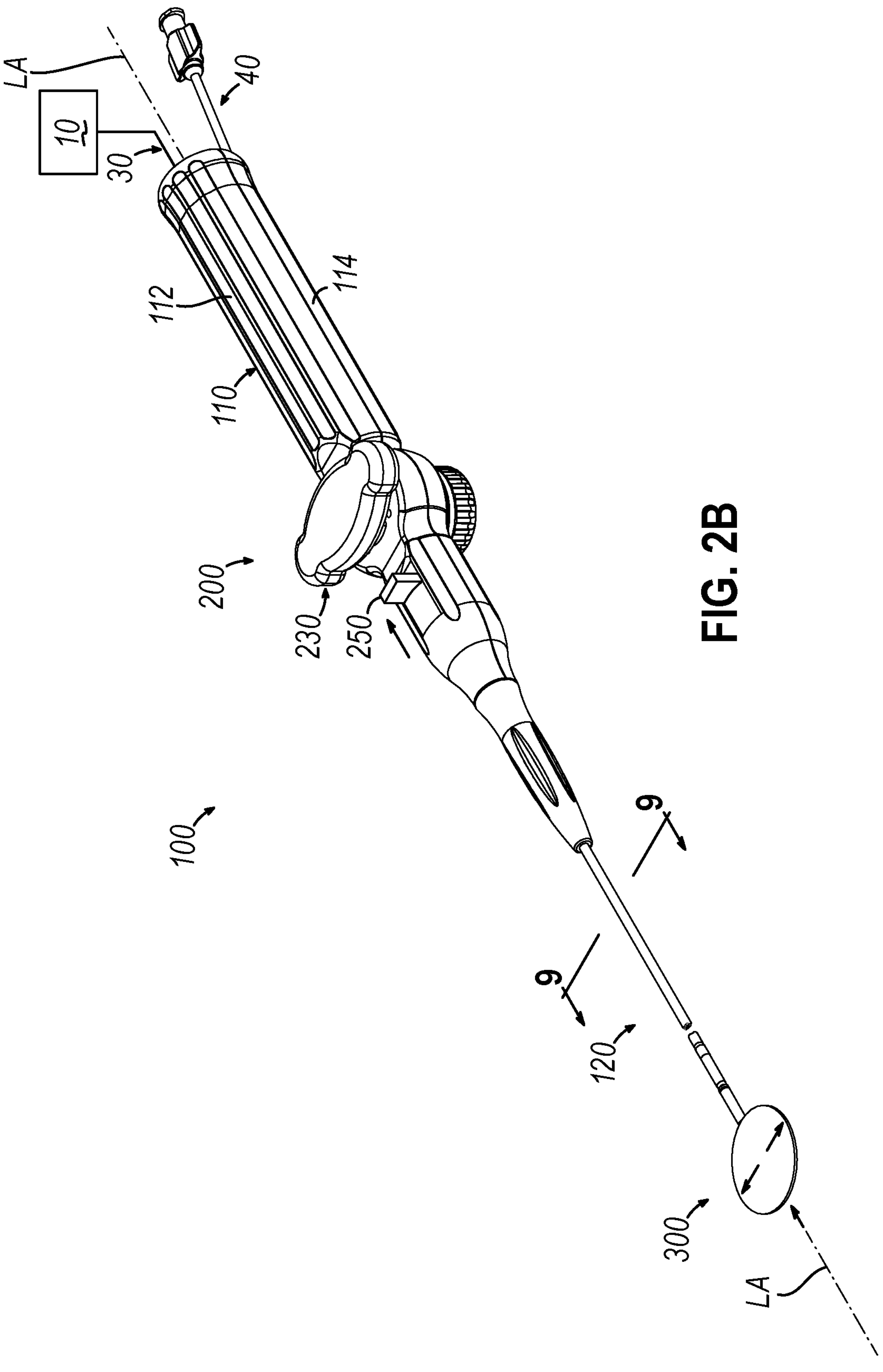
FIG. 2B depicts a perspective view of the catheter assembly of FIG. 1, with additional components shown in schematic form, and with the end effector in an expanded state.
Figure 3:
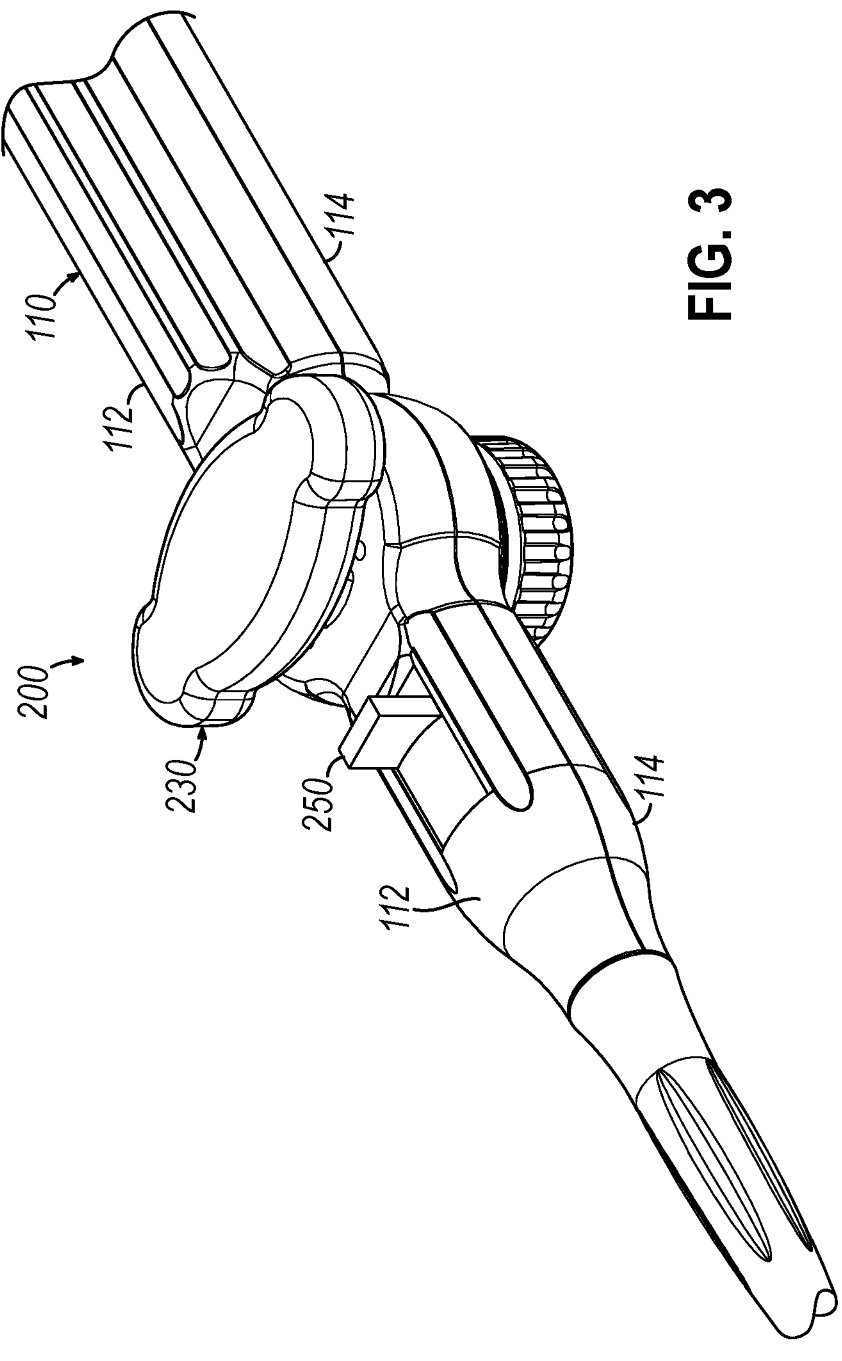
FIG. 3 depicts a perspective view of actuators on a handle assembly of the catheter assembly of FIG. 1.

FIG. 1 shows an exemplary medical procedure and associated components of a cardiac catheter system that may be used to provide EP mapping or cardiac ablation as referred to above. In particular, FIG. 1 shows a physician (PH) grasping a handle assembly (110) of a catheter assembly (100), with an end effector (300) of a catheter (120) (shown in FIGS. 2A-2B and 4 but not shown in FIG. 1) of catheter assembly (100) disposed in a patient (PA) to map potentials in tissue or ablate tissue in or near the heart (H) of the patient (PA). As shown in FIGS. 2A-3, catheter assembly (100) includes handle assembly (110), catheter (120) extending distally from handle assembly (110), end effector (300) located at a distal end of catheter (120), and a deflection drive assembly (200) associated with handle assembly (110).

As will be described in greater detail below, end effector (300) includes various components configured to deliver RF energy to targeted tissue sites, provide EP mapping functionality, track external forces imparted on end effector (300), track the location of end effector (300), or disperse irrigation fluid. As will also be described in greater detail below, deflection drive assembly (200) is configured to deflect end effector (300) and a distal portion of catheter (120) away from a central longitudinal axis (LA) defined by a proximal portion of catheter (120).

Figure 4:
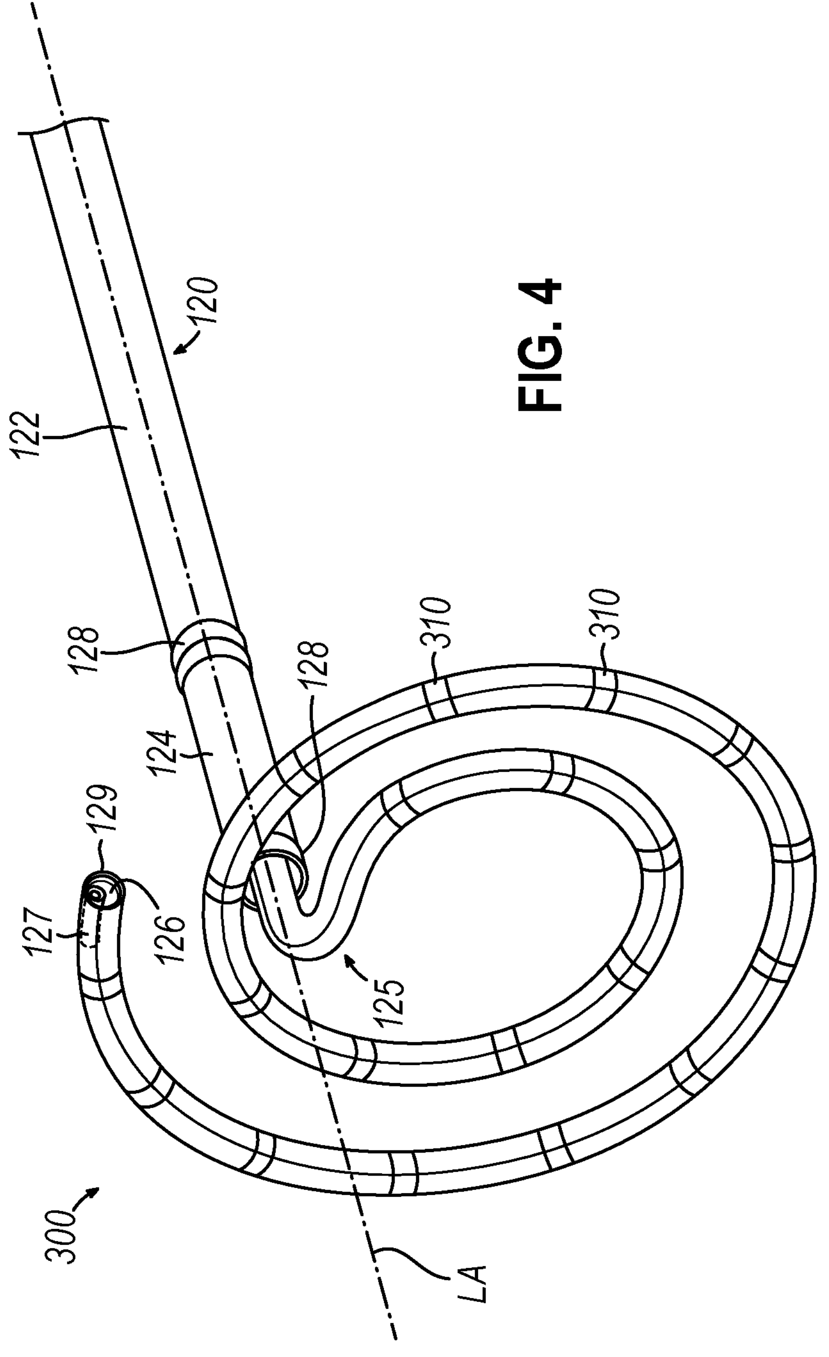
FIG. 4 depicts a perspective view of the end effector of FIG. 2A in the expanded state.

As shown in FIG. 4, catheter (120) includes an elongate flexible sheath (122), with end effector (300) being disposed at a distal end (125) of a first inner shaft (124) extending distally from sheath (122). End effector (300) and various components that are contained in sheath (122) will be described in greater detail below. Catheter assembly (100) is coupled with a guidance and drive system (10) via a cable (30). Catheter assembly (100) is also coupled with a fluid source (42) via a fluid conduit (40). A set of field generators (20) are positioned underneath the patient (PA) and are coupled with guidance and drive system (10) via another cable (22). Field generators (20) are merely optional.

Guidance and drive system (10) of the present example include a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via electrodes (310) of end effector (300) as described in greater detail below. Console (12) includes a processor (not shown) that processes such EP mapping signals and thereby provides EP mapping as is known in the art.

In versions where end effector (300) includes one or more ablation electrodes (not shown), first driver module (14) of the present example is further operable to provide RF power to such ablation electrodes, to thereby ablate tissue contacting the ablation electrodes. Second driver module (16) is coupled with field generators (20) via cable (22). Second driver module (16) is operable to activate field generators (20) to generate an alternating magnetic field around the heart (H) of the patient (PA). For instance, field generators (20) may include coils that generate alternating magnetic fields in a predetermined working volume that contains the heart (H).

First driver module (14) is also operable to receive position indicative signals from a navigation sensor assembly (127) in end effector (300). In such versions, the processor of console (12) is also operable to process the position indicative signals from navigation sensor assembly (127) to thereby determine the position of end effector (300) within the patient (PA). In some versions, navigation sensor assembly (127) includes two or more coils that are operable to generate signals that are indicative of the position and orientation of end effector (300) within the patient (PA). The coils are configured to generate electrical signals in response to the presence of an alternating electromagnetic field generated by field generators (20). Other components and techniques that may be used to generate real-time position data associated with end effector (300) may include wireless triangulation, acoustic tracking, optical tracking, inertial tracking, and the like. Alternatively, end effector (300) may lack a navigation sensor assembly (127).

Display (18) is coupled with the processor of console (12) and is operable to render images of patient anatomy. Such images may be based on a set of preoperatively or intraoperatively obtained images (e.g., a CT or MRI scan, 3-D map, etc.). The views of patient anatomy provided through display (18) may also change dynamically based on signals from navigation sensor assembly (127) of end effector (300). For instance, as end effector (300) of catheter (120) moves within the patient (PA), the corresponding position data from navigation sensor assembly (127) may cause the processor of console (12) to update the patient anatomy views in display (18) in real time to depict the regions of patient anatomy around end effector (300) as end effector (300) moves within the patient (PA). Moreover, the processor of console (12) may drive display (18) to show locations of aberrant conductive tissue sites, as detected via electrophysiological (EP) mapping with end effector (300) or as otherwise detected (e.g., using a dedicated EP mapping catheter, etc.). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (300) on the images of the patient's anatomy, such as by superimposing an illuminated dot, a crosshair, a graphical representation of end effector (300), or some other form of visual indication. Such a superimposed visual indication may also move within the images of the patient anatomy on display (18) in real time as the physician moves end effector (300) within the patient (PA), thereby providing real-time visual feedback to the operator about the position of end effector (300) within the patient (PA) as end effector (300) moves within the patient (PA). The images provided through display (18) may thus effectively provide a video tracking the position of end effector (300) within a patient (PA), without necessarily having any optical instrumentation (i.e., cameras) viewing end effector (300). In the same view, display (18) may simultaneously visually indicate the locations of aberrant conductive tissue sites detected through EP mapping. The physician (PH) may thus view display (18) to observe the real time positioning of end effector (300) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). As described in greater detail below, such irrigation fluid may be expelled through the open distal end (129) of a second inner shaft (126) of end effector (300). Such irrigation may be provided in any suitable fashion as will be apparent to those skilled in the art in view of the teachings herein.

II. Example of an End Effector

As shown in FIGS. 2A-2B, end effector (300) of the present example is operable to transition between a non-expanded state (FIG. 2A) and an expanded state (FIG. 2B). As will be described in greater detail below, this transitioning is driven by manipulation of an end effector expansion actuator (250) of handle assembly (110). In some versions, outer sheath (122) is configured to selectively slide over end effector (300) when end effector (300) is in the non-expanded state. In such versions, outer sheath (122) may be retracted proximally to expose end effector (300) to thereby enable end effector (300) to transition to the expanded state.

In the version depicted in FIGS. 2A-2B, end effector (300) is configured to define a bulbous or generally spherical shape when end effector (300) is in the expanded state. In such versions, end effector (300) may include an inflatable body (e.g., similar to a balloon). Alternatively, end effector (300) may include a plurality of strips or other structures that are configured to bow outwardly to define a bulbous or generally spherical shape when end effector (300) is in the expanded state. In such versions, the strips or other structures may define a generally cylindraceous shape or other substantially straight shape when end effector (300) is in the non-expanded state. The proximal end of each such strip or other structure may be fixedly secured relative to one shaft while the distal end of each such strip or other structure may be fixedly secured relative to another shaft. The strips or other structures may buckle and thereby bow outwardly in response to longitudinal translation of one of those shafts relative to the other of those shafts.

In the version depicted in in FIG. 4, end effector (300) is configured to define a spiral shape when in the expanded shape. End effector (300) of the example shown in FIG. 4 is mounted to first inner shaft (124), which is internal to outer sheath (122). End effector (300) of this example includes a plurality of electrodes (310). In some versions, electrodes (310) are operable to provide bipolar EP mapping by picking up electrocardiogram signals from tissue as is known in the art. Electrodes (310) may cooperate in pairs in some implementations. Signals picked up by electrodes (310) may be communicated back through electrical conduits (not shown) in catheter (120) to console (12), which may process the signals to provide EP mapping to thereby identify locations of aberrant electrical activity within the cardiac anatomy. This may in turn allow the physician (PH) to identify the most appropriate regions of cardiac tissue to ablate (e.g., with RF energy, cryoablation, etc.), to thereby prevent or at least reduce the communication of aberrant electrical activity across the cardiac tissue.

As also shown in FIG. 4, a pair of reference electrodes (128) are coaxially positioned about shaft (124). Such reference electrodes (128) may be utilized in conjunction with electrode pairs (330) during an EP mapping procedure. For instance, reference electrodes (128) may be utilized to pick up reference potentials from blood or saline that passes through the interior of end effector (300) during an EP mapping procedure. Such reference potentials may be used to reduce noise or far field signals, as is known in the art. In the present example, end effector (300) is configured such that reference electrodes (128) are positioned to avoid contacting tissue during use of end effector (300) in an EP mapping procedure; while still allowing blood and saline to flow freely through end effector (300) to reach reference electrodes (128).

By way of example only, electrodes (128, 332, 334) may be formed of platinum, gold, or any other suitable material. Electrodes (128, 332, 334) may include various coatings, if desired. For instance, electrode pairs (330) may include a coating that is selected to improve the signal-to-noise ratio of signals from electrode pairs (330). Such coatings may include, but need not be limited to, iridium oxide (IrOx) coating, poly(3,4-ethylenedioxythiophene) (PEDOT) coating, Electrodeposited Iridium Oxide (EIROF) coating, Platinum Iridium (PtIr) coating, or any other suitable coating. Various suitable kinds of coatings that may be used for electrodes (128, 332, 334) will be apparent to those skilled in the art in view of the teachings herein.

While only EP mapping electrodes (310) are shown in FIG. 4, other versions of end effector (300) may include ablation electrodes in addition to, or in lieu of, including EP mapping electrodes (310). Such ablation electrodes may be used to apply RF energy to tissue that is in contact with the ablation electrodes, to thereby ablate the tissue. Each ablation electrode may be coupled with a corresponding trace or other electrical conduit on end effector (300), thereby enabling console (12) to communicate RF energy through electrical conduits (not shown) in catheter (120) to the traces or other conduits on end effector (300) to reach the ablation electrodes.

End effector (300) of the present example further includes a position sensor (127) located near distal end (129) of second inner shaft (126). Position sensor (127) is operable to generate signals that are indicative of the position and orientation of end effector (300) within the patient (PA). By way of example only, position sensor (127) may be in the form of a wire coil or a plurality of wire coils (e.g., three orthogonal coils) that are configured to generate electrical signals in response to the presence of an alternating electromagnetic field generated by field generators (20). Position sensor (127) may be coupled with wire, a trace, or any other suitable electrical conduit along or otherwise through catheter (120), thereby enabling signals generated by position sensor (127) to be communicated back through electrical conduits (not shown) in catheter (120) to console (12). Console (12) may process the signals from position sensor (127) to identify the position of end effector (300) within the patient (PA). Other components and techniques that may be used to generate real-time position data associated with end effector (300) may include wireless triangulation, acoustic tracking, optical tracking, inertial tracking, and the like. In some versions, position sensor (127) may be omitted.

As noted above, catheter assembly (100) of the present example is coupled with a fluid source (42) via a fluid conduit (40). A fluid conduit (not shown) extends along the length of catheter (120) and is operable to deliver irrigation fluid (e.g., saline) out through the open distal end (129) of second inner shaft (126). For instance, the fluid conduit may distally terminate at distal end (129). In addition, or in the alternative, second inner shaft (126) may incorporate one or more laterally oriented irrigation ports that are in communication with the fluid conduit. Such irrigation ports may be spaced apart along the region of length corresponding to the longitudinal position of end effector (300). In either case, the irrigation fluid may provide cooling, flushing, or other effects at end effector (300) during operation of end effector (300) within the patient (PH). Various suitable ways in which catheter assembly (100) may provide irrigation will be apparent to those skilled in the art. Alternatively, some variations of catheter assembly (100) may lack irrigation capabilities, such that conduit (40), fluid source (42), and pump (44) may be omitted.

In addition to the foregoing, end effector (300) and other aspects of catheter assembly (100) may be configured and operable in accordance with at least some of the teachings of any one or more of the various patent documents that are incorporated by reference herein.

III. Example of End Effector Deflection Actuator

As noted above, catheter assembly (100) includes a deflection drive assembly (200) that is configured to deflect end effector (300) away from the central longitudinal axis (LA) defined by a proximal portion of catheter (120). Deflection drive assembly (200) of the present example incudes push-pull cables (162, 172), a cable driver assembly (210), and a rocker arm (230). As will be described in greater detail below, the physician (PA) may actuate rocker arm (230) relative to handle assembly (110) such that cable driver assembly (210) actuates push-pull cables (162, 172) in a simultaneous, longitudinally-opposing motion to selectively deflect end effector (300) laterally away from a longitudinal axis (LA), thereby enabling the physician (PH) to actively steer end effector (300) within the patient (PA).

Figure 7A:
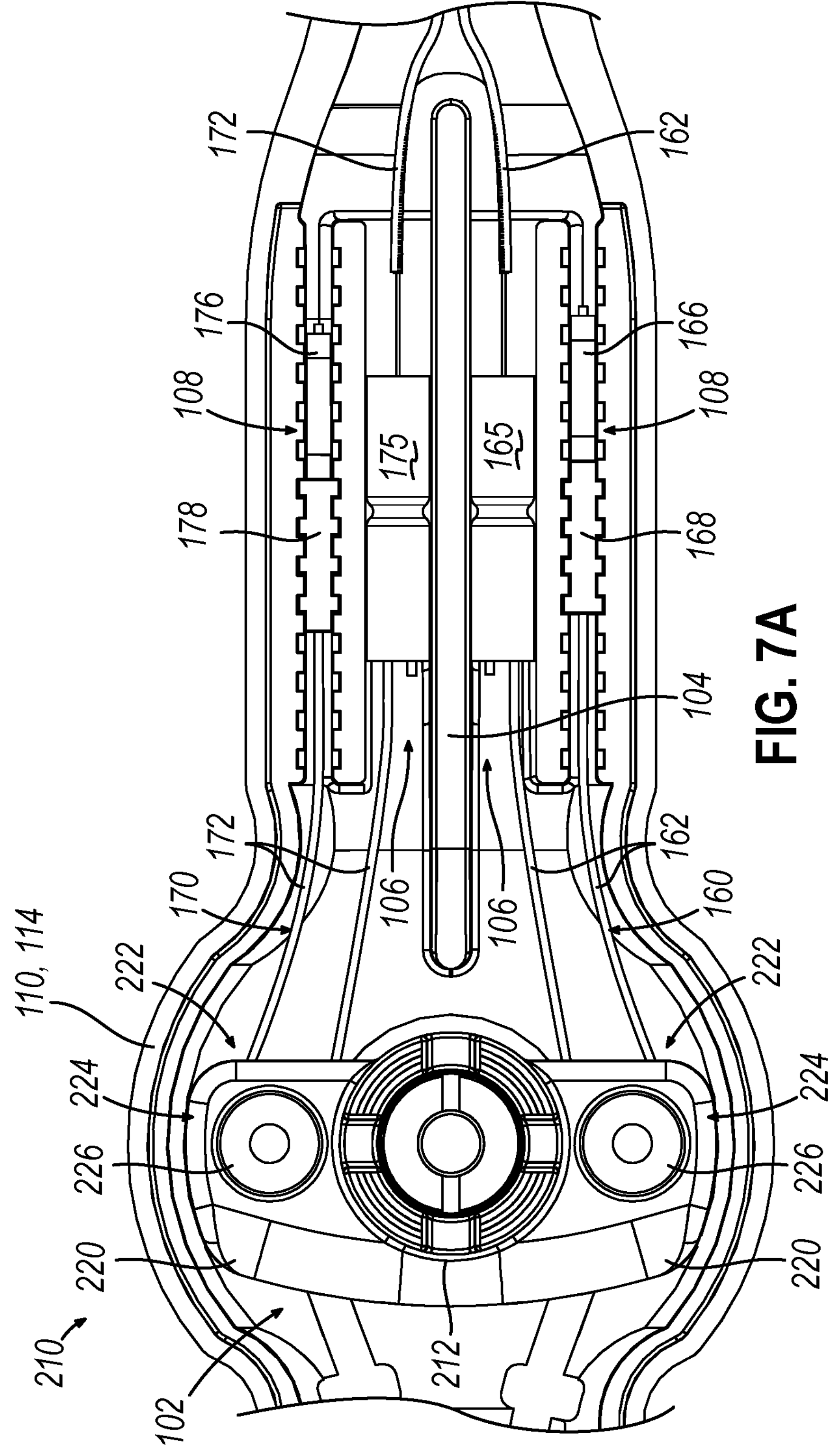
FIG. 7A depicts a top plan view of a portion of the handle assembly of FIG. 3, with a portion of the handle assembly omitted to reveal internal components, and with the articulation drive actuator in the first rotational position of FIG. 5A.
Figure 7B:
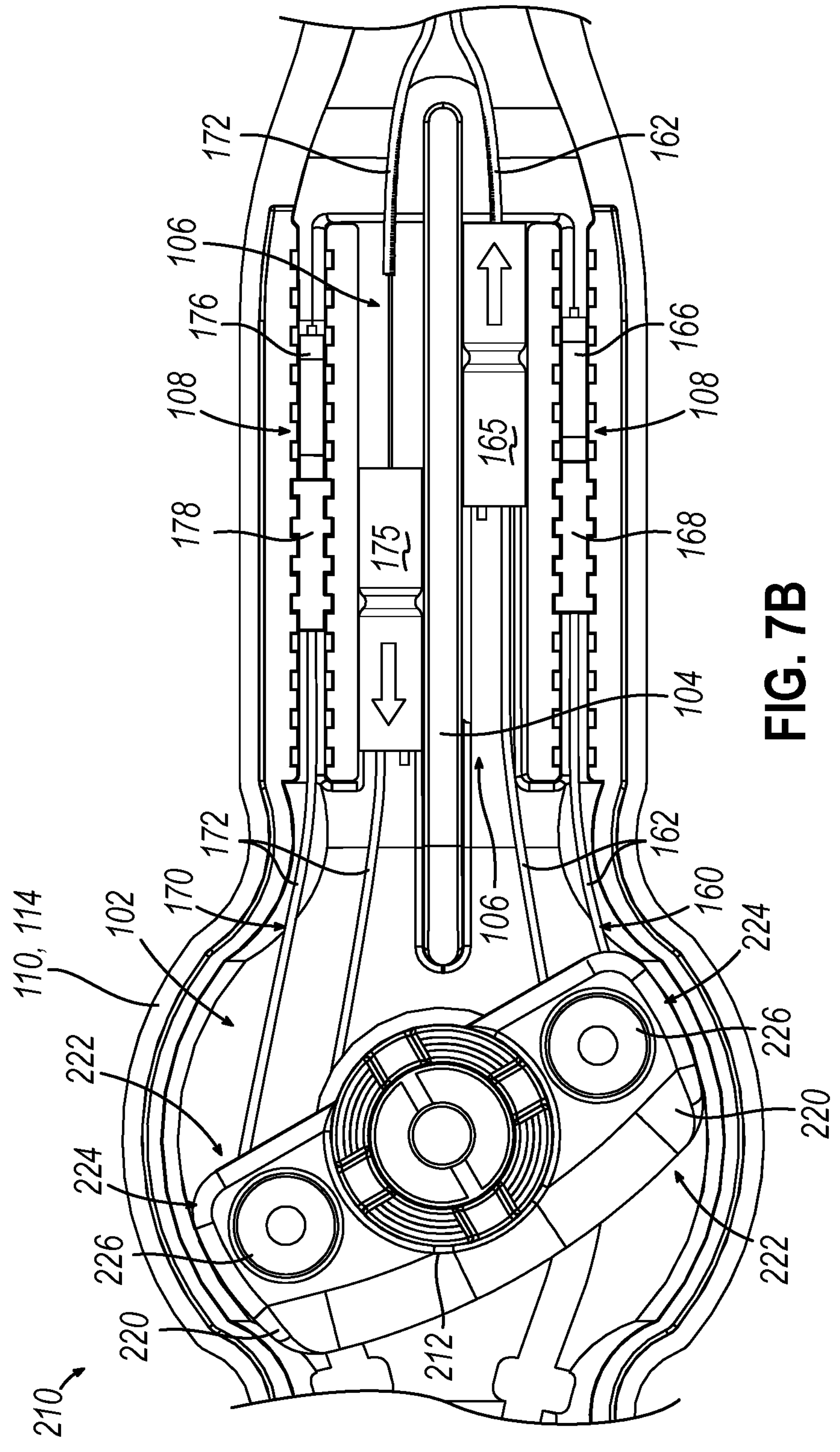
FIG. 7B depicts a top plan view of a portion of the handle assembly of FIG. 3, with a portion of the handle assembly omitted to reveal internal components, and with the articulation drive actuator in the second rotational position of FIG. 5B.
Figure 7C:
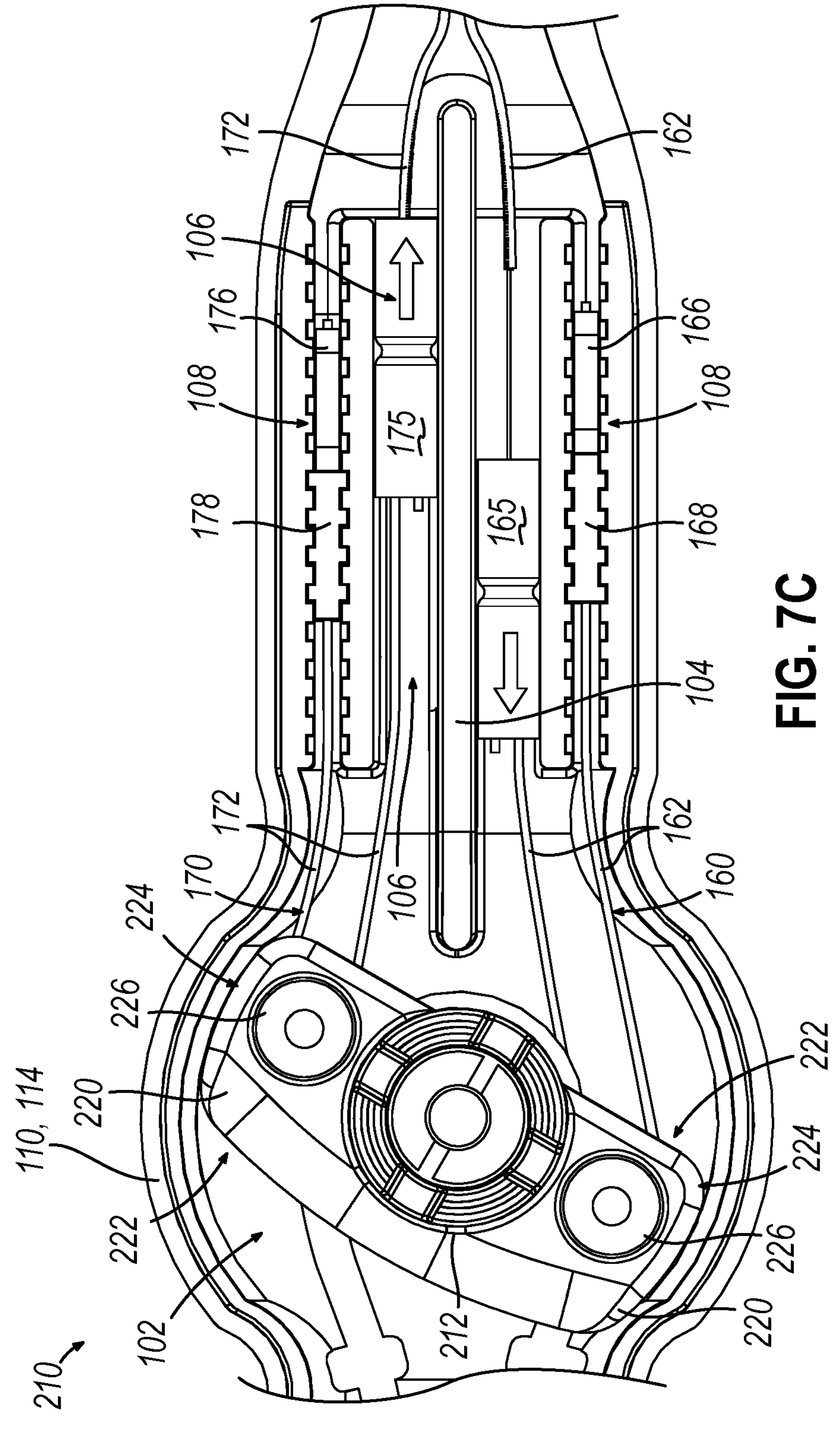
FIG. 7C depicts a top plan view of a portion of the handle assembly of FIG. 3, with a portion of the handle assembly omitted to reveal internal components, and with the articulation drive actuator in the third rotational position of FIG. 5C.

Selected portions of deflection drive assembly (200) are operatively coupled to handle assembly (110). As best seen in FIGS. 2A-3, handle assembly (110) includes a first casing portion (112) and a second casing portion (114). As best seen in FIGS. 7A-7C, casing portions (112, 114) together define an internal cavity (102). As also shown in FIGS. 7A-7C, a central body (212) of rocker arm (230) extends into cavity (102). A pair of lateral wings (220) extend outwardly from central body (212). Cable driver assembly (210) is rotationally coupled with handle assembly (110) such that cable driver (210) is configured to rotate about an axis that is perpendicular to the longitudinal axis (LA). As cable driver assembly (210) rotates, wings (220) orbit about the axis of rotation. This movement of wings causes simultaneous opposing translation of push-pull cables (162, 172) as described below.

Wings (220) of cable driver assembly (210) are configured to couple with a respective push-pull cable (162, 172) such that rotation of wings (220) about the axis of rotation of cable driver (210) will pull cables (162, 172) in accordance with the description herein. Each wing (220) defines a cable recess (222) and a plug opening (224) extending into cable recess (222). Cable recess (222) is dimensioned to receive intermediary portions of push-pull cables (162, 172), while plug opening (224) is dimensioned to receive cable plug (226) such that cable plug (226) actuates with wings (220). Cable recess (222) is dimensioned to accommodate cable plug (226) such that intermediary portions of push-pull cables (162, 172) may wrap around cable plug (226) as shown in FIGS. 7A-7C, thereby suitably coupling intermediary portions of push-pull cables (162, 172) with cable driver assembly (210). Cable plugs (226) interact with push-pull cables (162, 172) such that proximal movement of a cable plug (226) pulls the corresponding push-pull cable (162, 172) proximally.

An interior of second casing portion (114) includes a partition wall (104) and a pair of tension adjustment channels (108) located on opposite lateral sides of partition wall (104). Partition wall (104) and respective tension adjustment channels (108) together define a sliding channel (106). Each sliding channel (106) slidably houses a respective sliding body (165, 175). Sliding bodies (165, 175) are attached to respective push-pull cables (162, 172). Sliding bodies (165, 175) and sliding channels (106) may together assist in guiding the simultaneous opposing translation of portions of push-pull cables (162, 172) extending distally from sliding bodies (165, 175) in accordance with the description herein.

Tension adjustment channels (108) include a linear array laterally extending, rectangular projections. Tension adjustment channels (108) are configured to receive respective tension blocks (168, 178), which also each have a complementary linear array of laterally extending rectangular projections. The complementary rectangular projections of tensions blocks (168, 178) and tension adjustment channels (108) are configured to longitudinally fix tension blocks (168, 178) relative to second casing portion (114). In other words, tensions adjustment channels (108) are configured to receive tension blocks (168, 178) in a tongue-and-groove fashion to fix tension blocks (168, 178) relative to handle assembly (110). Tensions blocks (168, 178) may be selectively inserted along various suitable locations within adjustment channels (108) in order to serve as a mechanical ground for push-pull cables (162, 172). Tension blocks (168, 178) may be inserted along various locations within adjustment channels (108) in order to adjust the tension within push-pull cables (162, 172) to thereby accommodate for length variations of push-pull cables (162, 172) due to various factors, such as manufacturing tolerance variations, deformation of push-pull cables (162, 172), etc.

Push-pull cables (162, 172) are fixedly secured to respective proximal end blocks (166, 176). As best seen in FIGS. 7A-7C, proximal end blocks (166, 176) are housed within tension adjustment channels (108) just distal to tension blocks (168, 178). Tension blocks (168, 178) therefore prevent proximal end blocks (166, 176) from actuating proximally within adjustment channels (108), thereby serving as a mechanical ground for push-pull cables (162, 172). Tension blocks (168, 178) define a through hole that push-pull cables (162, 172) extend through such that push-pull cables (162, 172) may extend from proximal end blocks (166, 176) through adjustment channels (108) in order to suitably couple with cable driver assembly (210). Alternatively, tension blocks (168, 178) and respective proximal end blocks (166, 176) may be formed of a single piece.

Figures 5A, 6A:
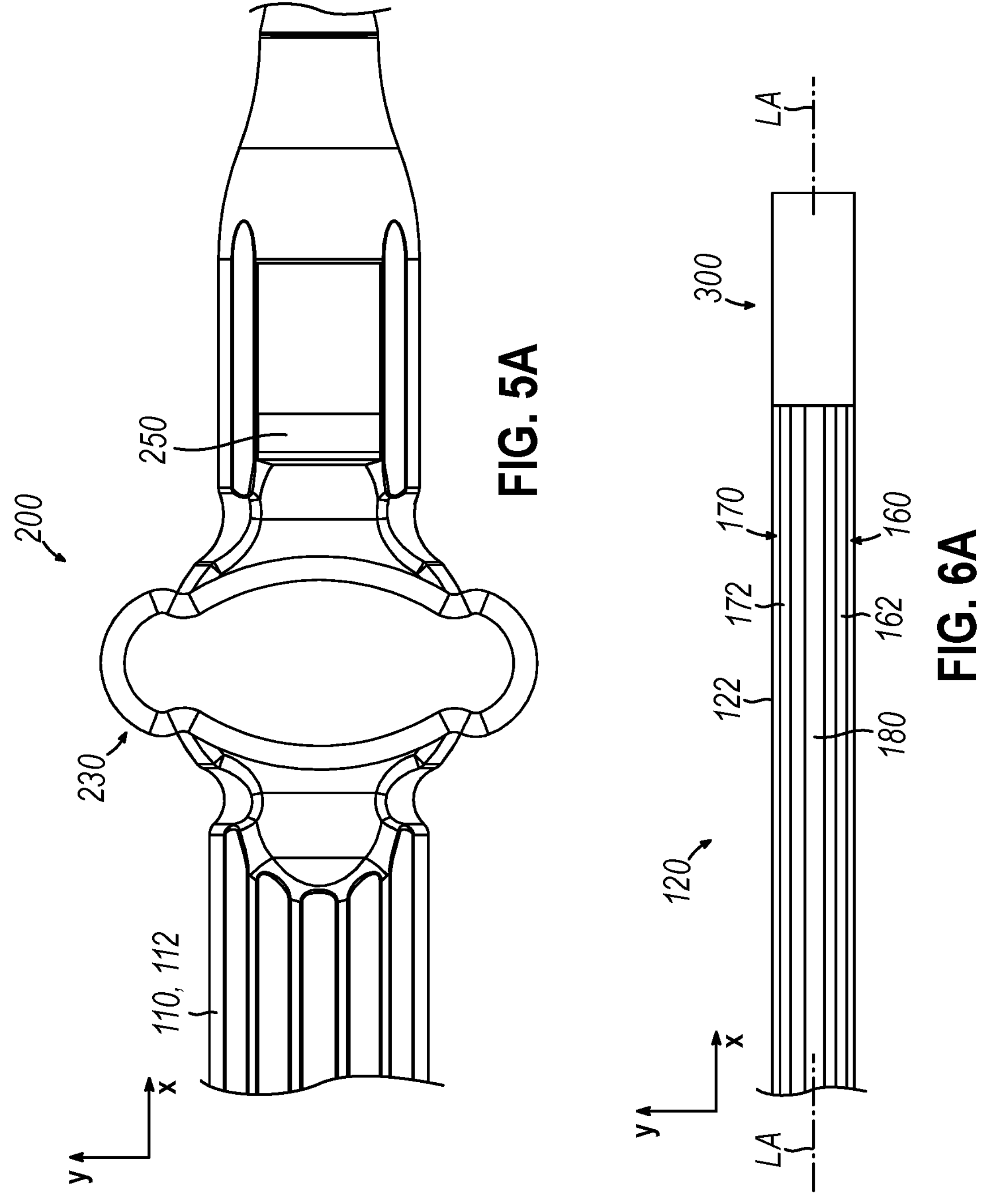
FIG. 5A depicts a top plan view of a portion of the handle assembly of FIG. 3, with an articulation drive actuator in a first rotational position.
FIG. 6A depicts a top plan view of the distal portion of the catheter of the catheter assembly of FIG. 1, with a portion of the catheter in cross-section, and with the distal portion in a non-deflected state associated with the first rotational position of the articulation drive actuator of FIG. 5A.
Figures 5B, 6B:
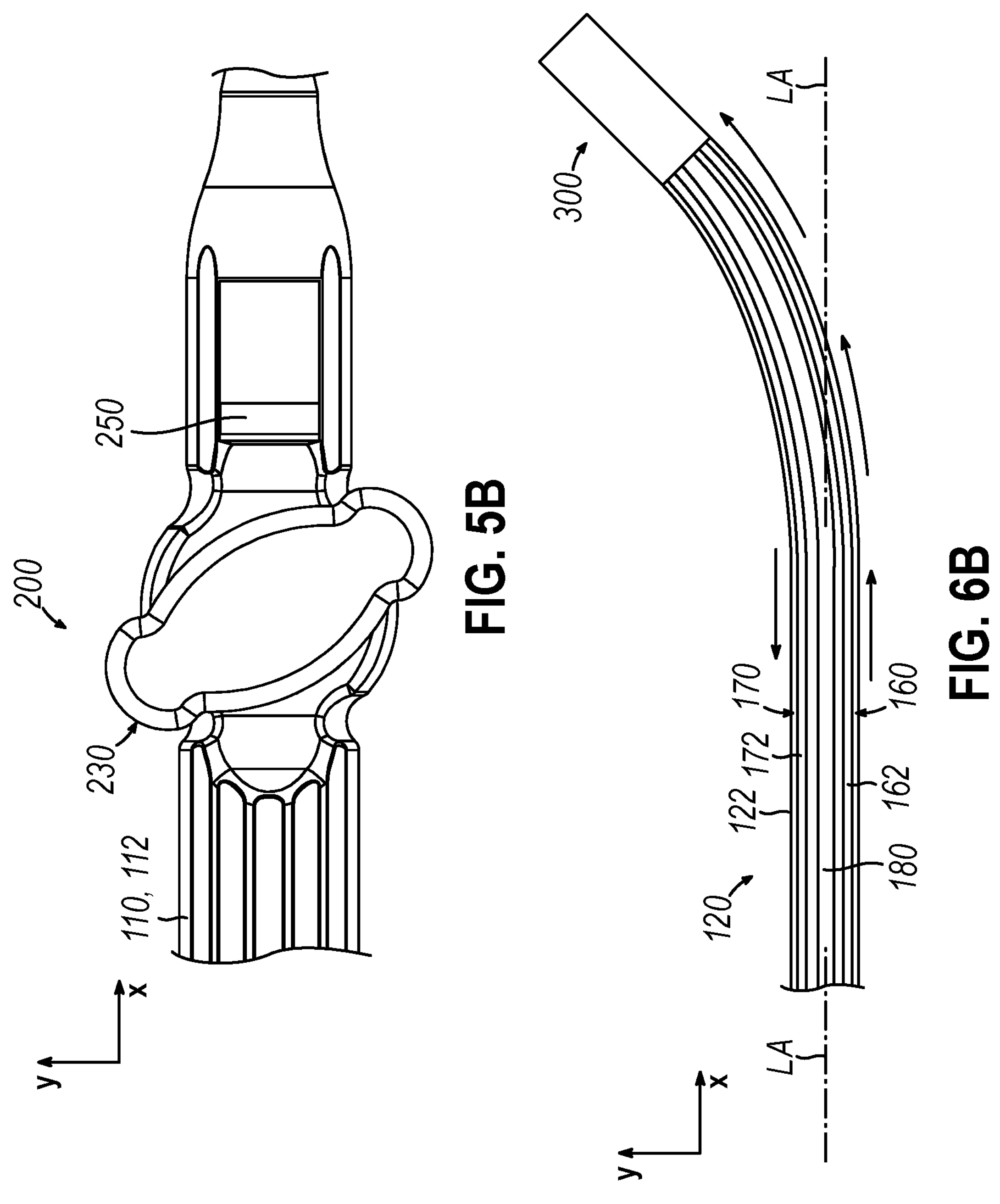
FIG. 5B depicts a top plan view of a portion of the handle assembly of FIG. 3, with the articulation drive actuator in a second rotational position
FIG. 6B depicts a top plan view of the distal portion of the catheter of FIG. 6A, with a portion of the catheter in cross-section, and with the distal portion in a first deflected state associated with the second rotational position of the articulation drive actuator of FIG. 5B.
Figures 5C, 6C:
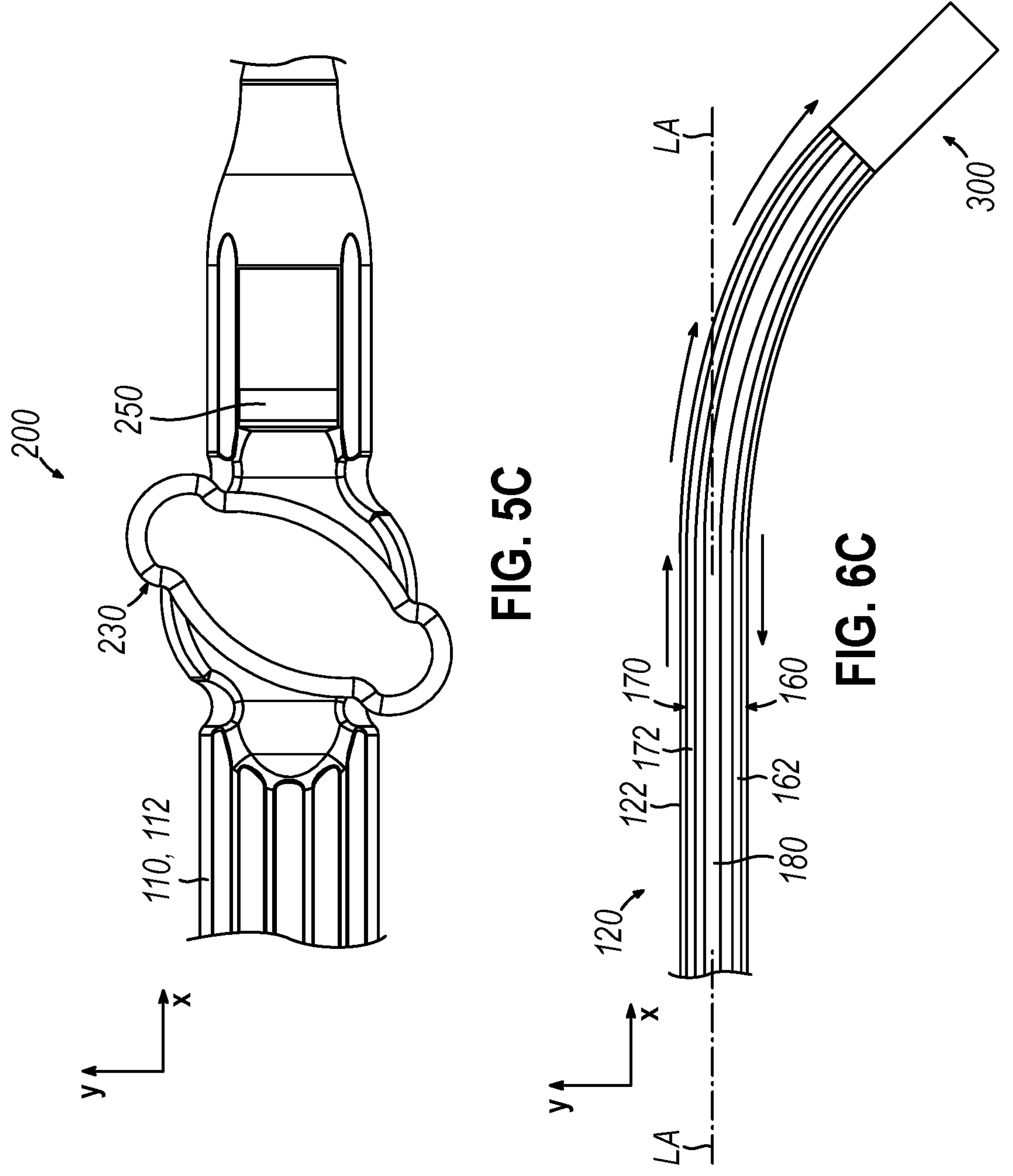
FIG. 5C depicts a top plan view of a portion of the handle assembly of FIG. 3, with the articulation drive actuator in a third rotational position.
FIG. 6C depicts a top plan view of the distal portion of the catheter of FIG. 6A, with a portion of the catheter in cross-section, and with the distal portion in a second deflected state associated with the third rotational position of the articulation drive actuator of FIG. 5C.

As best shown in FIGS. 6A-6C, the distal ends of push-pull cables (162, 172) are coupled with end effector (300). Various suitable ways in which push-pull cables (162, 172) may be coupled with end effector (300) will be apparent to those skilled in the art in view of the teachings herein.

FIGS. 5A-6C show exemplary use of deflection drive assembly (200) to deflect end effector (300) and the distal portion of catheter (120) away from the central longitudinal axis (LA). FIGS. 5A and 6A show various sections of catheter assembly (100) when end effector (300) is in a neutral, non-deflected position. FIG. 5A shows rocker arm (230) in a neutral rotational position relative to handle assembly (110). As best shown in FIG. 7A, when rocker arm (230) is in the first rotational position, cable driver assembly (210) is in a corresponding first rotation position such that sliding bodies (165, 175), and therefore push-pull cables (162, 172), are in a first longitudinal position associated with end effector (300) being in the non-deflected position as shown in FIG. 6A.

When the physician (PH) desires to deflect end effector (300) in a first direction relative to central longitudinal axis (LA) to a first deflected position shown in FIG. 6B, the physician (PH) may rotate rocker arm (230) relative to casing portions (112, 114) to the position shown in FIG. 5B. As best shown in FIG. 7B, rotation of rocker arm (230) to the rotational position shown in FIG. 5B drives cable driver assembly (210) into a corresponding rotational position such that plug (226) associated with push-pull cable (170) drives push-pull cable (170) proximally. Additionally, plug (226) associated with push-pull cable (160) is driven distally, allowing push-pull cable (160) to actuate distally.

Proximal translation of push-pull cable (170) drives sliding body (175) proximally within the respective sliding channel (106), which also allows sliding body (165) to slide distally within sliding channel (106). Proximal translation of sliding body (175) drives the section of intermediate portion (172) extending distally from sliding body (175), as well as distal portion (174), proximally. Since distal portion (174) may not actuate proximally out of end effector (300), as described above, proximal translation of distal portion (174) drives end effector (300) to bend to the position shown in FIG. 6B.

Similarly, when the physician (PH) desires to deflect end effector (300) in a section direction relative to central longitudinal axis (LA) to a second deflected position shown in FIG. 6C, the physician (PH) may rotate rocker arm (230) relative to handle assembly (110) to the position shown in FIG. 5C. As best shown in FIG. 7C, rotation of rocker arm (230) to the rotational position shown in FIG. 5C drives cable driver assembly (210) into a corresponding rotational position such that plug (226) associated with push-pull cable (160) drives push-pull cable (160) proximally. Additionally, plug (226) associated with push-pull cable (170) is driven distally, allowing push-pull cable (170) to actuate distally.

Proximal translation of push-pull cable (160) drives sliding body (165) proximally within sliding channel (106), which also allows sliding body (175) slide distally within sliding channel (106). Proximal translation of sliding body (165) drives the section of intermediate portion (162)

extending distally from sliding body (165), as well as distal portion (164), proximally. Since distal portion (164) may not actuate proximally out of end effector (300), as described above, proximal translation of distal portion (164) drives end effector (300) to bend to the position shown in FIG. 6C.

In some versions, catheter assembly (100) is operable to deform catheter (120) such that end effector (300) is deflected a full 180 degrees. In other words, the distal portion of catheter (120) may be bent by push-pull cables (162, 172) to a point where end effector (300) is oriented proximally, along an axis that is parallel with yet laterally offset from the longitudinal axis (LA). Various suitable ways in which such a 180-degree bend angle may be achieved will be apparent to those skilled in the art in view of the teachings herein. It should also be understood that such 180-degree bending may be provided bi-directionally, such that end effector (300) may be deflected to the left a full 180 degrees or to the right a full 180 degrees.

In the foregoing examples, rotation of rocker arm (230) about an x-y plane (as shown in FIGS. 5A-5C results in lateral deflection of end effector (300) away from the longitudinal axis (LA), with the deflection also being along the x-y plane. In some other versions, end effector (300) deflects along the x-z plane, in addition to or as an alternative to deflecting along the x-y plane. Various other suitable mechanisms that may be used to drive push-pull cables (162, 172) in a simultaneous, longitudinally-opposing fashion will be apparent to those skilled in the art in view of the teachings herein. Similarly, various other suitable mechanisms that may be used to drive lateral deflection of end effector (300) away from the longitudinal axis (LA) will be apparent to those skilled in the art in view of the teachings herein.

IV. Example of End Effector Expansion Actuator

Figure 8A:
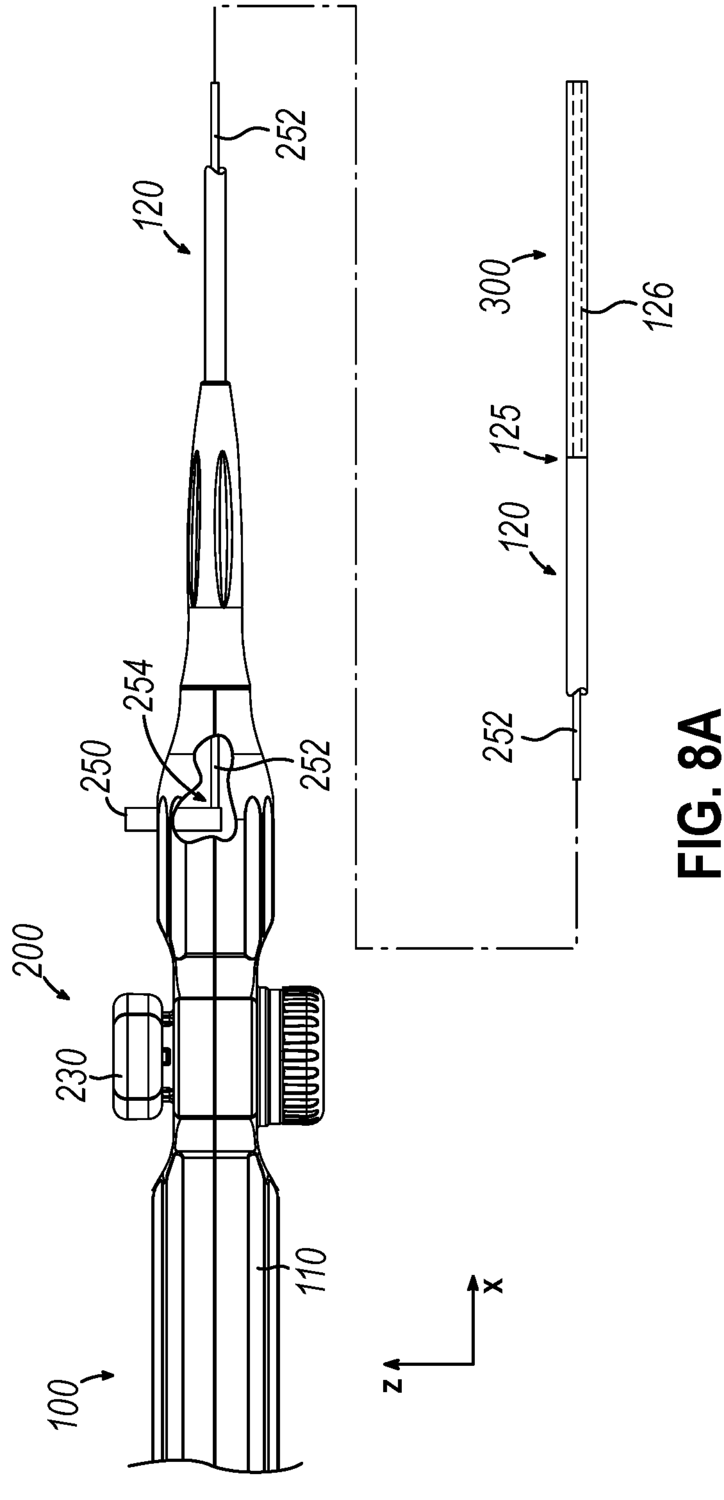
FIG. 8A depicts a side elevational view of the catheter assembly of FIG. 1, with a portion of the handle assembly broken away to reveal internal components, with an end effector expansion actuator in a first longitudinal position, and with the end effector in a non-expanded state.
Figure 8B:
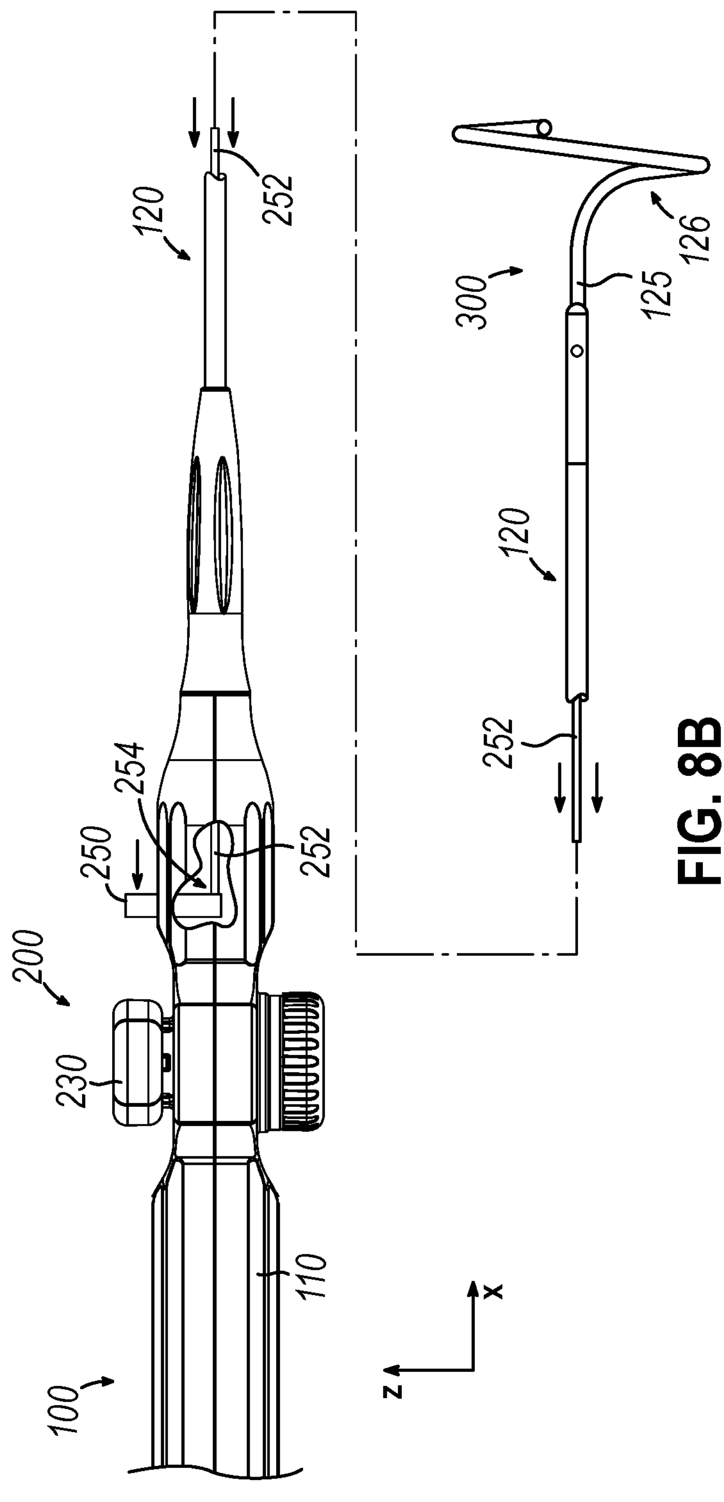
FIG. 8B depicts a side elevational view of the catheter assembly of FIG. 1, with a portion of the handle assembly broken away to reveal internal components, with the end effector expansion actuator in a second longitudinal position, and with the end effector in an expanded state.

As shown in FIGS. 2A-2B and FIGS. 8A-8B, end effector expansion actuator (250) is operable to drive end effector (300) to transition between a non-expanded state (FIGS. 2A and 8A) and an expanded state (FIGS. 2B and 8B). End effector expansion actuator (250) of the present example is in the form of a slider that is operable to translate longitudinally relative to casing portions (112, 114) between a distal position (FIGS. 2A and 8A) and a proximal position (FIGS. 2B and 8B). End effector expansion actuator (250) is coupled with end effector (300) via a push-pull cable (252), which extends along the length of catheter (120). A proximal end of push-pull cable (252) is coupled with a base (254) of end effector expansion actuator (250). A distal end of push-pull cable (252) is coupled with a corresponding component of end effector (300). Various suitable ways in which push-pull cable (252) may be coupled with end effector expansion actuator (250) and second inner shaft (126) will be apparent to those skilled in the art in view of the teachings herein.

It should be understood from the foregoing that longitudinal translation of end effector expansion actuator (250) is communicated to second inner shaft (126) via push-pull cable (252). As noted above, since the distal end of end effector (300) is secured to second inner shaft (126) and the proximal end of end effector (300) is secured to first inner shaft (124), longitudinal translation of second inner shaft (126) relative to first inner shaft (124) will cause end effector (300) to transition from a non-expanded state to an expanded state, or to transition from an expanded state to a non-expanded state, depending on the direction of translation of first inner shaft (124).

In some variations, at least a portion of end effector (300) is resiliently biased to urge end effector (300) toward the expanded state shown in FIGS. 2B, 4, and 8B. In some such versions, the resilience of end effector (300) may assist push-pull cable (252) and second inner shaft (126) in driving end effector (300) toward the expanded state. In some other versions, push-pull cable (252) drives the entire length of end effector (300) distally or proximally relative to outer sheath (122). In such versions, outer sheath (122) may compress end effector (300) to reach a non-expanded state when end effector (300) is proximally positioned within outer sheath (122); while the resilience of end effector (300) drives end effector (300) to the expanded state when end effector (300) is positioned distally from outer sheath (122). Other suitable ways in which end effector (300) may transition between the expanded state and the non-expanded state will be apparent to those skilled in the art in view of the teachings herein. Similarly, other suitable ways in which push-pull cable (252) may be utilized will be apparent to those skilled in the art in view of the teachings herein.

V. Example of Shaft Features

It may be desirable to ensure that, when end effector (300) moves away from or toward the longitudinal axis (LA) in response to rotation of rocker arm (230), the motion of end effector (300) is confined to the x-y plane. In other words, it may be desirable to ensure that end effector (300) does not also deflect along the x-z plane when end effector (300) deflects along the x-y plane. To that end, it may be desirable to provide reinforcement within catheter (120) to ensure that end effector (300) only deflects along one single plane without also deflecting along another plane. An example of such a reinforcement is shown in FIG. 9, which depicts a cross-sectional view of catheter (120) taken along line 9-9 of FIG. 2A.

Figure 9:
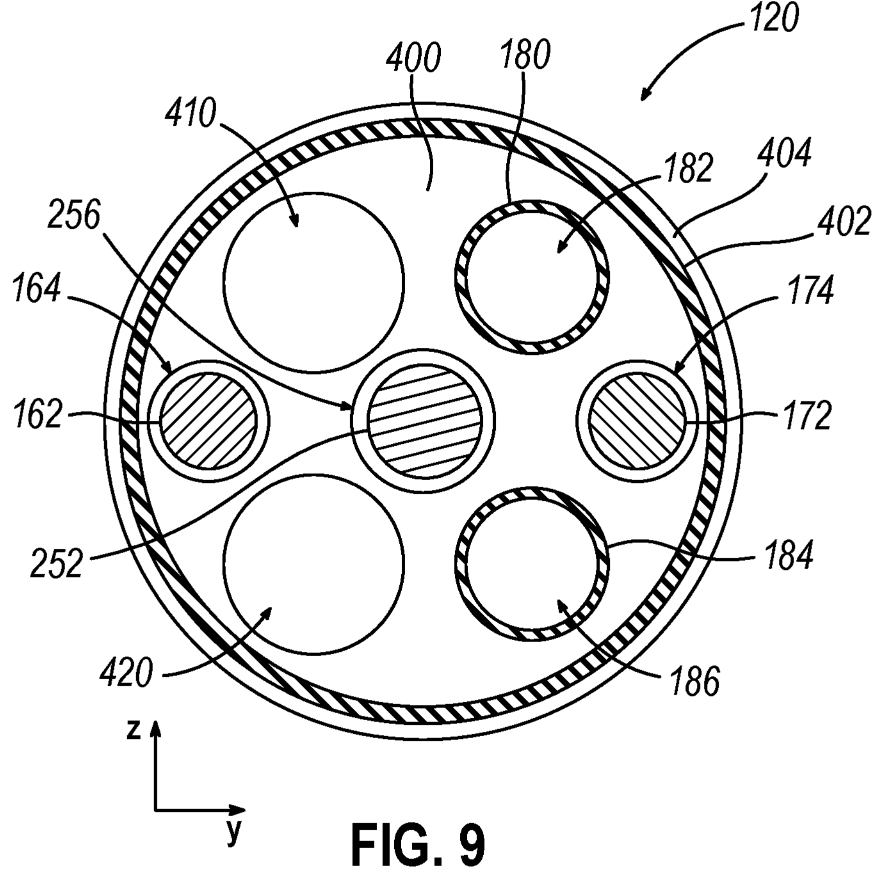
FIG. 9 depicts a cross-sectional view of the catheter of FIG. 6A, taken along line 9-9 of FIG. 2A.

As shown in FIG. 9, catheter (120) of the present example includes a tubular body (400) with a total of seven lumens (164, 174, 182, 186, 256, 410, 420) formed therein. Lumens (164, 174, 182, 186, 256, 410, 420) extend along the entire length of body (400). By way of example only, tubular body (400) may be formed of pellethane, pebax, nylon, or any other suitable material(s). A first outer sheath (402) is coaxially positioned about body (400); while a second outer sheath (404) is coaxially positioned about first outer sheath (402). In some versions, first outer sheath (402) is formed of a braided material, such as braided steel or braided polymeric fibers. By way of example only, first outer sheath (402) may be configured to provide substantial torsional strength to catheter (120), facilitating rotation of catheter (120) about the longitudinal axis (LA) without resulting in substantial winding or torsional build-up in catheter (120). Also in some versions second outer sheath (404) is formed of a polymeric material. By way of example only, second outer sheath (404) may be the same as outer sheath (122) described above. Alternatively, outer sheath (122) may be coaxially disposed about at least a portion of second outer sheath (404).

Lumen (164) of the present example is configured to accommodate push-pull cable (162). Similarly, lumen (174) is configured to accommodate push-pull cable (172). Lumens (164, 174) are laterally offset from each other along the y-axis, such that lumens (164, 174) and push-pull cables (162, 172) are collectively positioned along the x-y plane. Lumen (182) includes a tubular insert (180); while lumen (186) also includes a tubular insert (184). Tubular inserts (180, 184) extend along the length of shaft (120). Lumens (182, 186) are laterally offset from each other along the z-axis, such that lumens (182. 186) and tubular inserts (180, 184) are collectively positioned along the x-z plane. With lumens (164, 174) and push-pull cables (162, 172) being collectively positioned along the x-y plane, and lumens (182. 186) and tubular inserts (180, 184) being collectively positioned along the x-z plane, it may be said that push-pull cables (162, 172) and tubular inserts (180, 184) are orthogonally oriented relative to each other, even though push-pull cables (162, 172) and tubular inserts (180, 184) all extend along the x-dimension.

In the present example, tubular inserts (180, 184) are formed of a material that has greater rigidity than the material forming body (400), such that tubular inserts (180, 184) serve as struts. Tubular inserts (180, 184) may be formed of any suitable material, including but not limited to polyimide. Moreover, tubular inserts (180, 184) may be co-extruded with body (400). Alternatively, tubular inserts (180, 184) may be formed in any other suitable fashion.

In the present example, due to the material of tubular inserts (180, 184) having greater stiffness or rigidity than the material of body (400), and due to the orthogonal positioning of push-pull cables (162, 172) versus tubular inserts (180, 184), tubular inserts (180, 184) are configured to prevent deflection of catheter (120) along the x-z plane. In other words, when push-pull cables (162, 172) are actuated to deflect end effector (300) and the distal portion of catheter (120) laterally along the x-y plane, tubular inserts (180, 184) ensure that such deflection is confined to the x-y plane without any additional deflection occurring along the x-z plane. By ensuring that the deflection of end effector (300) and the distal portion of catheter (120) is only along a single plane, tubular inserts (180, 184) may provide greater consistency and predictability in the operation of catheter assembly (100).

Lumen (256) of the present example is configured to accommodate push-pull cable (252). While lumen (256) is slightly offset from the radial center of body (400) in the present example, other versions may provide lumen (256) in the radial center of body (400). Even with lumen (256) and push-pull cable (252) being slightly offset from the radial center of body (400) in the present example, lumen (256) and push-pull cable (252) are close enough to the radial center of body (400) such that actuation of push-pull cable (252) does not apply a substantial eccentric load to body (400) when the distal end of catheter (120) and end effector (300) are in a laterally deflected state.

Lumen (410) of the present example is configured to accommodate wires (not shown). Such wires may be coupled with various electrical components in end effector (300), such as electrodes (128, 310), position sensor (127), or any other components. Such wires may be braided, bundled, or otherwise arranged within lumen (256). Lumen (420) of the present example is configured to provide a path for fluid communication along the length of catheter (120). In particular, lumen (420) may provide a path for irrigation fluid from fluid source (42) and fluid conduit (40) to the open distal end (129) of a second inner shaft (126) of end effector (300). While lumens (410, 420) are shown as having similarly sized diameters, other versions may provide a lumen (410) that is larger than lumen (420); or a lumen (420) that is larger than lumen (410).

Despite having seven lumens (164, 174, 182, 186, 256, 410, 420) and the other structural features described above, catheter (120) may have a substantially small outer diameter. By way of example only, catheter (120) may have an outer diameter less than or equal to approximately 8.5 French. Alternatively, catheter (120) may have any other suitable outer diameter.

VI. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a handle; (b) a catheter extending distally from the handle, a proximal portion of the catheter defining a longitudinal axis, the catheter including: (i) a body, the body defining: (A) a first lumen, (B) a second lumen, and (C) a third lumen; (ii) a first cable positioned in the first lumen, the first cable being operable to translate relative to the body of the catheter, (iii) a second cable positioned in the second lumen, the second cable being operable to translate relative to the body of the catheter, and (iv) a third cable positioned in the third lumen, the third cable being operable to translate relative to the body of the catheter; and (c) an end effector extending distally from the catheter, the end effector including at least one electrode.

Example 2

The apparatus of Example 1, the handle including a first actuator, the first actuator being operable to drive the first cable to thereby translate the first cable longitudinally relative to the body of the catheter.

Example 3

The apparatus of Example 2, the first actuator being further operable to drive the second cable to thereby translate the second cable longitudinally relative to the body of the catheter.

Example 4

The apparatus of Example 3, the first actuator being operable to drive the first cable to translate in a first direction longitudinally relative to the body of the catheter while simultaneously driving the second cable to translate in a second direction longitudinally relative to the body of the catheter, the second direction being opposite to the first direction.

Example 5

The apparatus of any one or more of Examples 2 through 4, the handle including a handle body, the first actuator being rotatable relative to the handle body.

Example 6

The apparatus of Example 5, the first actuator comprising a rocker arm.

Example 7

The apparatus of any one or more of Examples 2 through 6, the handle further including a second actuator, the second actuator being operable to drive the third cable to thereby translate the third cable longitudinally relative to the body of the catheter.

Example 8

The apparatus of Example 7, the handle including a handle body, the second actuator being translatable relative to the handle body.

Example 9

The apparatus of Example 8, the second actuator comprising a slider.

Example 10

The apparatus of any one or more of Examples 1 through 9, the end effector being configured to transition between a non-expanded state and an expanded state.

Example 11

The apparatus of Example 10, the end effector being configured to define a cylindraceous shape in the non-expanded state, the end effector being configured to define a generally spherical or spiral shape in the expanded state.

Example 12

The apparatus of any one or more of Examples 10 through 11, the third cable being operable to drive the end effector to transition from the non-expanded state to the expanded state.

Example 13

The apparatus of Example 12, the third cable being further operable to drive the end effector to transition from the expanded state to the non-expanded state.

Example 14

The apparatus of any one or more of Examples 1 through 13, the end effector including a flexible body with a plurality of strips.

Example 15

The apparatus of any one or more of Examples 1 through 14, the end effector including a plurality of electrophysiology mapping electrodes configured to sense potentials in tissue.

Example 16

The apparatus of any one or more of Examples 1 through 15, the end effector including a position sensor configured to generate a signal indicating a position of the end effector in three-dimensional space.

Example 17

The apparatus of any one or more of Examples 1 through 16, the end effector being operable to dispense fluid.

Example 18

The apparatus of Example 17, the body of the body of the catheter further defining a fourth lumen, the fourth lumen being in fluid communication with the end effector such that the fourth lumen is operable to communicate fluid from a fluid source to the end effector.

Example 19

The apparatus of any one or more of Examples 1 through 17, the body of the catheter further defining a fourth lumen and a fifth lumen, the catheter further including a first strut and a second strut, the first strut being fixedly secured in the fourth lumen, the second strut being fixedly secured in the fifth lumen.

Example 20

The apparatus of Example 19, the first and second struts having greater rigidity than the body of the catheter.

Example 21

The apparatus of any one or more of Examples 19 through 20, the first and second cables being positioned along a first plane, the first and second struts being positioned along a second plane, the second plane being orthogonal to the first plane.

Example 22

The apparatus of Example 21, the first and second cables being operable to deflect the end effector laterally along the first plane, away from the longitudinal axis.

Example 23

The apparatus of Example 22, the first and second struts being configured to prevent deflection of the end effector along the second plane, away from the longitudinal axis.

Example 24

The apparatus of any one or more of Examples 1 through 23, the body of the catheter further defining: (A) a fourth lumen, (B) a fifth lumen, (C) a sixth lumen, and (D) a seventh lumen.

Example 25

The apparatus of Example 24, the fourth lumen containing a first strut, the fifth lumen containing a second strut, the sixth lumen defining a pathway for communication of fluid to the end effector, and the seventh lumen containing one or more wires extending to the end effector.

Example 26

An apparatus, comprising: (a) a handle; (b) a catheter extending distally from the handle, a proximal portion of the catheter defining a longitudinal axis, the catheter including: (i) a body, the body defining: (A) a first lumen, (B) a second lumen, (C) a third lumen, and (D) a fourth lumen, (ii) a first cable positioned in the first lumen, the first cable being operable to translate relative to the body of the catheter, (iii) a second cable positioned in the second lumen, the second cable being operable to translate relative to the body of the catheter, (iv) a first strut positioned in the third lumen, the first strut having greater rigidity than the body of the catheter, and (v) a second strut positioned in the fourth lumen, the second strut having greater rigidity than the body of the catheter, the first and second cables being positioned along a first plane, the first and second struts being positioned along a second plane, the second plane being orthogonal to the first plane; and (c) an end effector extending distally from the catheter, the end effector including at least one electrode.

Example 27

The apparatus of Example 26, the first and second cables being operable to deflect the end effector laterally away from the longitudinal axis, along the first plane.

Example 28

The apparatus of Example 27, the first and second cables being operable to deflect the end effector from a straight position laterally in a first direction away from the longitudinal axis, along the first plane; the first and second cables being further operable to deflect the end effector from the straight position laterally in a second direction away from the longitudinal axis, along the first plane.

Example 29

The apparatus of any one or more of Examples 26 through 28, the catheter further comprising a third cable positioned in a fifth lumen defined by the body of the catheter, the third cable being operable to translate relative to the body of the catheter.

Example 30

The apparatus of Example 29, the third cable being operable to drive the end effector to transition from a non-expanded state to an expanded state.

Example 31

An apparatus, comprising: (a) a handle; (b) a catheter extending distally from the handle, a proximal portion of the catheter defining a longitudinal axis, the catheter including a body defining: (i) a first lumen, (ii) a second lumen, (iii) a third lumen, (iv) a fourth lumen, (v) a fifth lumen, (vi) a sixth lumen, and (vii) a seventh lumen; (c) an end effector extending distally from the catheter, the end effector including at least one electrode.

Example 32

The apparatus of Example 31, the catheter further comprising: (i) a first cable disposed in the first lumen, and (ii) a second cable disposed in the second lumen, the first and second cables being operable to deflect the end effector away from the longitudinal axis.

Example 33

The apparatus of Example 32, the catheter further comprising a third cable disposed in the third lumen, the third cable being operable to translate relative to the body of the catheter.

Example 34

The apparatus of Example 33, the third cable being operable to drive the end effector to transition from a non-expanded state to an expanded state.

Example 35

The apparatus of any one or more of Examples 33 through 34, the catheter further comprising: (i) a first strut disposed in the fourth lumen, the first strut having greater rigidity than the body of the catheter, and (ii) a second strut disposed in the fifth lumen, the second strut having greater rigidity than the body of the catheter.

Example 36

The apparatus of Example 35, the first and second lumens being positioned along a first plane, the fourth and fifth lumens being positioned along a second plane, the second plane being orthogonal to the first plane.

Example 37

The apparatus of any one or more of Examples 35 through 36, the catheter further comprising one or more wires disposed in the sixth lumen, the one or more wires being coupled with the end effector.

Example 38

The apparatus of Example 37, the seventh lumen being configured to provide a path for communication of fluid from a fluid source to the end effector.

Example 39

The apparatus of any one or more of Examples 33 through 38, the catheter further comprising a braided member coaxially disposed about the body of the catheter.

Example 40

The apparatus of any one or more of Examples 33 through 39, the catheter having an outer diameter less than or equal to approximately 8.5 French.

VII. Miscellaneous

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:

(a) a catheter, a proximal portion of the catheter defining a longitudinal axis, the catheter having an outer diameter of about 8.5 French or smaller and including:

(i) a first shaft with a first shaft lumen;

(ii) a second shaft extending through the first shaft lumen, and configured for longitudinal translation relative to the first shaft, the second shaft defining:

(A) first and second lumens defining a first plane coextensive with the longitudinal axis;

(B) a third lumen between the first and second lumens and intersected by the first plane;

(C) fourth and fifth lumens defining a second plane orthogonal to the first plane;

(D) a sixth lumen defining a pathway for communication of fluid; and (E) a seventh lumen;

(iii) a first cable positioned in the first lumen, the first cable being operable to translate relative to the second shaft;

(iv) a second cable positioned in the second lumen, the second cable being operable to translate relative to the second shaft; and (v) a third cable positioned in the third lumen, the third cable being operable to translate relative to the first shaft;

(vi) a first tubular insert positioned in the fourth lumen; and (vii) a second tubular insert positioned in the fifth lumen;

(viii) one or more wires extending through the seventh lumen;

(b) an end effector extending distally from the second shaft, the end effector including at least one electrode and configured to transition between an expanded configuration and a non-expanded configuration, distal ends of the first and second cables coupled to the end effector; and (c) a handle at a proximal end of the catheter, the handle comprising:

(ix) a deflection drive assembly comprising a rocker arm coupled to the first and second cables such that rotation of the rocker arm results in simultaneous and opposite translational movement of the first and second cables, the first and second cables being operable in response to the rotation of the rocker arm to deflect the end effector laterally along the first plane, away from the longitudinal axis upon actuation of the deflection drive assembly, the first and second tubular inserts configured with greater rigidity than the second shaft to prevent deflection of the end effector along the second plane, away from the longitudinal axis; and (x) an end effector expansion actuator comprising a slider and a base, the slider configured for direct operation by a user to move translationally between a proximal position and a distal position, the slider being coupled to the base, and the base being coupled to a proximal end of the third cable, the slider being positioned distal of the rocker arm of the deflection drive assembly such that the proximal end of the third cable terminates distal of the rocker arm, a distal end of the third cable being coupled to the end effector, the slider configured to move between a first position that moves the end effector into the expanded configuration when distal of a distal end of the first shaft, and a second position that returns the end effector into the first shaft lumen of the first shaft in the non-expanded configuration.

2. The apparatus of claim 1, the end effector being configured to define a cylindraceous shape in the non-expanded configuration, the end effector being configured to define a generally spherical or spiral shape in the expanded configuration.

3. The apparatus of claim 1, the end effector including a flexible body with a plurality of strips.

4. The apparatus of claim 1, the end effector including a plurality of electrophysiology mapping electrodes configured to sense potentials in tissue.

5. The apparatus of claim 1, the end effector comprising at least one opening configured to dispense the fluid from the sixth lumen.

6. The apparatus of claim 1, the fourth and fifth lumens being closer to one of the first and second lumens than to the other of the first and second lumens.

7. The apparatus of claim 1, one of the fourth and fifth lumens being closer to the seventh lumen than the other of the fourth and fifth lumens.

* * * * *